(12) United States Patent
Wang et al.

(10) Patent No.: US 8,883,032 B2
(45) Date of Patent: Nov. 11, 2014

(54) METHOD OF SURFACE TREATMENT FOR ZIRCONIA DENTAL IMPLANTS

(71) Applicant: Taipei Medical University, Taipei (TW)

(72) Inventors: Sea-Fue Wang, Taipei (TW);
Chung-Kuang Yang, Taipei (TW);
Jen-Chang Yang, Taipei (TW);
Sheng-Yang Lee, Taipei (TW)

(*) Notice: Subject to any disclaimer, the term of this patent is extended or adjusted under 35 U.S.C. 154(b) by 0 days.

(21) Appl. No.: 13/687,212

(22) Filed: Nov. 28, 2012

(65) Prior Publication Data

US 2014/0144880 A1 May 29, 2014

(51) Int. Cl.
*C03C 15/00* (2006.01)
*B44C 1/22* (2006.01)

(52) U.S. Cl.
CPC .................... *B44C 1/227* (2013.01)
USPC ............ 216/96; 216/99; 216/102; 433/201.1; 433/172; 433/176

(58) Field of Classification Search
USPC ............ 216/96, 99–102; 433/201.1, 172–176
See application file for complete search history.

(56) References Cited

U.S. PATENT DOCUMENTS

| 8,408,906 B2* | 4/2013 | de Wild et al. ............. 433/201.1 |
| 2005/0106534 A1* | 5/2005 | Gahlert ........................ 433/173 |

OTHER PUBLICATIONS

Piascik et al. Dental Materials, vol. 28, (2012), pp. 604-608.*

\* cited by examiner

*Primary Examiner* — Duy Deo
*Assistant Examiner* — Maki Angadi
(74) *Attorney, Agent, or Firm* — McClure, Qualey & Rodack, LLP

(57) ABSTRACT

A method of surface treatment for zirconium oxide implants and the etching formula for the same are disclosed. The processes are carried out at room temperature. The average surface roughness Ra and the standard deviation of the implant are measured showing significant improvement while comparing with the un-treated sample and the hydrofluoric acid treated samples. The average contact angle is provided showing an almost hydrophilic surface after etched by the formula according to the present invention.

8 Claims, 5 Drawing Sheets

(i) (ii)

(iM) (iiM)

(iii)

(iiiM)

METHOD OF SURFACE TREATMENT FOR ZIRCONIA DENTAL IMPLANTS

FIELD OF THE INVENTION

The present invention relates to a surface treatment on zirconia dental implants, in particular, to a method of surface treatment by an etching processing.

DESCRIPTION OF THE PRIOR ART

With aging or improper use, some of the teeth pathological phenomena such as dental caries, attrition, and periodontitis may occur. Severe dental caries or periodontal disease can lead to tooth extraction. Long-term dental loss may cause the alveolar bone resorption and affect the functions of bite, chew, pronunciation, aesthetics etc. Conventional clinical treatments for patient include removable and fixed dentures. The foregoing conventional dental treatments have their individual disadvantages. For instance, for installing fixed dentures, It usually involves grinding down healthy teeth adjacent to the space as pillars to support the missing teeth.

In the dental development, a first titanium implant placed into the body of the animal in 1981 by Per-Ingvar Brånemark, and his team found that the implant and hard tissue are closely attached after a period of healing. He then proposed the osseointegration concept. After that, a dental implant for those patients who have dental defect is an effective healing method and become an indispensable healing candidate in the dental field.

Recently, due to the concept prompt in aesthetics and biomimetics, the number of patients who choose metal-free treatment increases. Dental biomaterials may be classified into ceramics, metals, polymers and composites. Among them, the ceramic material is found to have superior properties in hardness, biocompatibility and chemical stability. Among them, zirconia ceramics gain attentions due to its ivory color. The surface of implant will direct contact with the surrounding tissue cells. The surface roughness and the hydrophilic properties are found to affect cell adhesion thereby affecting the osseointegration and the success of dental surgery.

Although it is beneficial to the surrounding tissue of the alveolar bone for a zirconia dental implant with appropriate surface treatment. The surface modification to the zirconia by chemical treatment is, however, difficult since the zirconia is a material of acid-resist.

The conventional processes of the surface treatment include sandblasting firstly and then following by etching the blasted implant with an etching solution or by a casting mold with cavities formed so that the ceramic implant will inherit its microscopic roughness after unloading the mold and then the implant is then etched in an etching solution.

An exemplary embodiment refers to U.S. patent publication No 20080261178, with a title "Process for Providing a Topography to the Surface of a Dental Implant," by Hommann et al., who discloses the pretreatments including a sandblast with a pressure of 4 to 10 bar, milling and/or forming the predetermined roughness in the casting mold or the injecting mold. Thereafter, the implant is etched in an etching solution with an etching temperature at least 70 for short etching time. In fact, the etching temperature is between about 102~104 and an etching solution contains at least 50 vol. % HF to remove loosen particles or agglomerates. The processes of sandblasting and etching may repeat several times to generate significant numbers of pits on the surface of the implant.

Another conventional technology, please refer to an U.S. patent publication No. 20100042223, with a title of "Method of Surface Finishing, a Bone Implant" disclosed by Olivier Zinger et al. The processes comprise the steps of roughening a surface of the implant by blasting with abrasive particles and then etching the surface-roughened implant in an etching solution with ultrasonic oscillation in order to loosen any partially embedded abrasive blasting particles that may be contaminating the surface of the implant. The etching time to loosen the abrasive blasting particles is about several tens to several hundreds of seconds. The etching process does not intent to generate extra roughness. The etching solution per liter contains 50 g $(NH_4)HF_2$, and 400 ml 65% $HNO_3$.

Further conventional reference is disclosed on US patent publication No. 20090176191 by Gahlert et al., with a title "Ceramic Dental Implant," Gahlert et al., asserts: when the dental implant in the region of the anchoring part has a maximum surface roughness preferably between 2 and 15 μm, in particularly preferred between 6 and 12 μm. The processes comprises sandblasting treatment, and then etching the sand-blasted implant in an etching solution of phosphoric acid of 15 to 50 vol. %, in particularly preferred 20 to 40 vol. %. The etching time is very short about 10 sec to 10 min. Preferably, the time is between 15 and 60 sec.

The object of fast etching process as foregoing two patent applications depicting is to remove any abrasive blasting particles embedded in the blessed implant so as to avoid the abrasive particles contaminating the implant. That is, the object of the etching is to avoid the abrasive particles further flowing into the newly recess or pores, which are formed the etching process with the etching solution.

Since the abrasive particles are pressed on the surface of implants by exerting pressure so that some of unfortunate particles may be embedded into the implants but do not be removed completely during the pickling process. Thereafter, when the contaminated implant is placed into a body of the patient, it may cause the victim inflame easily. Apart from that, the mechanical stress may generate scratches onto the surface of the implant, which may weaken the mechanical strength such as fatigue property deterioration if the scratches are happened at the cleavage plane of the ceramic implants.

Alternatively to the sandblasting, if the macroscopic roughness formed on the surface of an implant is provided by a casting mold with surface cavities, then a poor mold unloading may occur.

In views of the problems of the prior art, an object of the present invention is thus to provide a method of surface treatment for a zirconia dental implant by chemical acid erosion to generate surface roughness so as to facilitate alveolar bone tissue cells ding and shorten the recovery time of the patient after surgery.

SUMMARY OF THE INVENTION

An object of the present invention is to provide a method of surface treatment for a zirconia dental implant by chemical acid erosion to generate surface roughness so as to facilitate bone tissue cells cling.

The composition of the etching solution for a ceramic zirconia implant or disk comprises a mixture of hydrofluoric acid 55~60 vol. %, phosphoric acid 20~45 vol. % and deionized water for the remnant. The other etching conditions include etching at room temperature for 12~24 hours. In particular, the pretreatment before etching does not include sandblasting milling or surface roughness treatment to the casting or injecting mold.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1A:
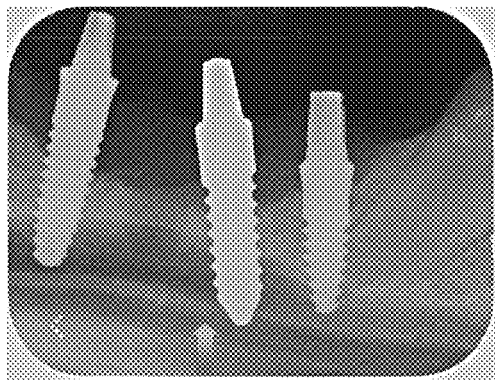
FIGS. 1A and 1B show x ray photograph of dental implant implanted in a maxilla and a mandible, respectively according to the present invention.

In a preferred embodiment, the surface treatment of a zirconia sample is performed at room temperature using an acidic solution having a composition comprising a mixture of 60 vol. % hydrofluoric acid and 40 vol. % phosphoric acid. After etching, the surface morphology of the zirconia disk presents a uniform surface roughness and a contact angle of about 5° or less in average with a standard deviation (STD) of about 2° or beyond, which means the surface of the zirconia disk almost completely hydrophilic. Thus, it is beneficial to shorten osseointegration time after the implant surgery.

For facilitating the contact angles measurement, zirconia ceramic disk samples of about Ø15 mm in diameter and 2 mm in thickness are used. The zirconia ceramic disks are formed of zirconia powder mixed with 3 mole % of $Y_2O_3$ pressed in a mold and sintered.

Firstly, the zirconia disk samples are degreased in an acetone. Thereafter, the samples are etched in the acidic solution tank at a temperature 25° C. The samples #1 to #3 are etched for 12 hours and the samples #1 to #3 are etched for 24 hours. All of the acidic solutions contain 60 vol. % HF but add with different volume fractions of $H_3PO_4$, respectively, such as 0 vol. % 40 vol. %, and 20 vol. % $H_3PO_4$. Thereafter, the contact angle of every sample is measured. Table I shows the results:

TABLE I

| Sample No. | Temperature (° C.) | time (h) | HF (vol. %) | $H_3PO_4$ (vol. %) | DI-water (vol. %) | Contact Angle (°) | STD (°) |
|---|---|---|---|---|---|---|---|
| 1 | 25 | 12 | 60 | — | 40 | 45.2 | 7.9 |
| 2 | 25 | 12 | 60 | 40 | — | 30.5 | 4.3 |
| 3 | 25 | 12 | 60 | 20 | 20 | 40.1 | 6.5 |
| 4 | 25 | 24 | 60 | — | 40 | 10.1 | 9.9 |
| 5 | 25 | 24 | 60 | 40 | — | 4.3 | 1.3 |
| 6 | 25 | 24 | 60 | 20 | 20 | 6.5 | 4.1 |

By comparing the samples from #1 to #6, it is found that the average contact angles measured after long term (24 hours etching time) is better than that of short term (12 hours) etching no matter an etching solution of HF whether adding phosphoric acid or not. The contact angle is defined as an equilibrium contact angle between solid-liquid interfacial energy and liquid-gas interfacial energy. In table I, the contact angle pairs (sample pairs) of 45.2° (#1) vs. 10.1° (#4), 30.5° (#2) vs. 4.3° (#5), and 40.1° (#3) vs. 6.5° (#6) are listed herein for antithesis. The samples etched by the etching solution of HF adding $H_3PO_4$ can further down the average contact angle to 4.3 and 6.5° for samples #5 and #6, respectively. The standard deviation of the sample #5 is only 1.3°. Thus, it proves that an etching solution containing the phosphoric acid has an effect of roughness increase and prompts uniform distribution of etching pits.

For purpose of comparing whether a higher etching temperature beneficial to shorten the etching time, the experiments are carried out at a temperature of 104° C. for 25 min In an exemplary embodiment, the etching solution contains different volume fractions of HF for etching the samples is performed. The results are show in table II.

Worthwhile, though the temperature is the same as the prior art, such as the Hommann's reference, the pretreatment of the samples herein do not include sandblasting process. All the samples #7~#10 are untreated.

TABLE II

| Sample No. | Temperature (° C.) | time (min) | HF (vol. %) | DI water (vol. %) | Contact Angle (°) | STD (°) |
|---|---|---|---|---|---|---|
| 7 | 104 | 25 | 10 | 90 | 80.2 | 6.5 |
| 8 | 104 | 25 | 40 | 60 | 71.1 | 4.4 |
| 9 | 104 | 25 | 60 | 40 | 67.4 | 7.5 |
| 10 | untreated | — | — | — | 93.1 | 4.9 |

The results of table II show the increase of the concentration of HF is beneficial to the decrease of the contact angle. Nevertheless, the decrease of contact angle of the samples in table II is poor than those of samples shown in the table I under the same concentration of HF. For example, by comparing the sample #9 to the sample #1, corresponding contact angles of 67.4° vs 45.2° are found.

Therefore, in comparison with the results shown in table I and table II, the compositions of the etching solutions associated with room etching temperature shown in table I according to the present invention indeed can gain many benefits including significantly reduce the contact angle and very low or free from any potential risk of the prior arts, which suggest using a sandblasting method, milling, and/or using a casting mold having macroscopic roughness thereon and then high etching temperature for a very short time etching. The sandblasting method may weaken the fatigue property of the implant or having risk of residual abrasive particles embedded in the implant body.

Figure 1B:
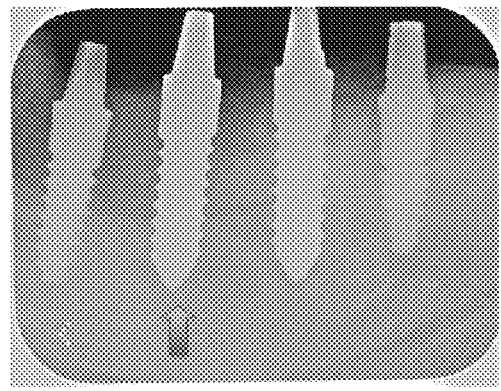

Note, in the foregoing experimental data, the zirconia ceramic samples using disk rather than implant is to facilitate the contact angle analysis. To further analyze the clinic effect of the dental implant is placed within the animal. The surface of zirconia ceramic implants is etched at a temperature of 25° C. for 24 hours using an etching solution having a composition comprising a mixture of 60 vol. % HF, and 40 vol. % $H_3PO_4$. The dental implant is formed of zirconia powder mixed with 3 mole % of $Y_2O_3$ pressed in a mold and sintered. The surface treated dental implants, and untreated dental implants are then placed into the maxilla and mandible of the Lanyu mini pigs for 8 weeks and 16 weeks and then analyzed. The FIG. 1A and FIG. 1B show X-rays photo of maxilla and mandible, respectively. Thereafter, the resonant frequency evaluation is carried out by using Impramate, which is a dental implant solid analyzer manufactured by BioTechOne under conditions of the probe and the samples are mutual perpendicular. The data of resonant frequency will be automatically fetched and averaged per three duty cycles. Five measurements are further made for taking their final average. The results are shown in table III.

TABLE III (resonant frequency securely firm analysis)

| | weeks | maxilla (un-treated) | maxilla (treated) | mandible (un-treated) | mandible (treated) |
|---|---|---|---|---|---|
| average resonant frequency (kHz) | 8 | 8.33 ± 1.30 | 10.65 ± 1.89 | 11.27 ± 0.78 | 11.26 ± 0.77 |
| | 16 | 10.68 ± 1.06 | 11.11 ± 1.91 | 10.88 ± 1.13 | 11.51 ± 2.35 |

According to principle of the resonant frequency, the more securely firm an implanted implant is, the higher a fed back frequency will be. Furthermore, if the resonant frequency of the implanted implant up to 10 kHz in the initial firm, it means the implant can withstand immediate load.

Analyzing the data shown in table III, it is found that the surface treated implant placed within the maxilla has a significant effect on the recovery period up to 8 weeks from 16 weeks according to the fed-back resonant frequency of the surface treated implant after 8 weeks placed within the bone is equivalent to that of the untreated implant after 16 weeks. The performance of the implant is found improve with the healing time. The resonant frequency is up to 11.11±1.91 kHz for 16 weeks, from 10.65±1.89 kHz for 8 weeks, as shown in table III. The performance of the implant placed in the mandible presents very good effect after 16 weeks of healing period no matter whether the surface treated implant or the untreated implant. However, the effect of the surface treated implant is about the same as the untreated implant. Though the value of 11.51 kHz is better than 10.88 kHz but the difference may be seen as insignificant according to the statistics.

Further, a bone to implant volume (BIV) analysis is performed for the specimens harvested from in vivo animal study by using the Micro-CT for surface treated implant using the etching conditions the same as the sample 5 in table I. The results are shown in table IV.

TABLE IV (BIV bone volume analysis)

| | weeks | maxilla (un-treated) | maxilla (treated) | mandible (un-treated) | mandible (treated) |
|---|---|---|---|---|---|
| Average contact bone volume (%) | 8 | 38.74 ± 1.42 | 43.22 ± 1.2 | 39.29 ± 2.77 | 41.27 ± 2.43 |
| | 16 | 39.87 ± 2.95 | 43.33 ± 1.45 | 43.08 ± 0.88 | 42.27 ± 1.64 |

The higher the BIV value is the better osseointegration of the dental implant with the alveolar bone will be. According to the results shown in table IV. The performance is quite similar to the resonant frequency analysis shown in table III. The healing period can be shorten to 8 weeks from 16 weeks when the surface treated implant is placed in the maxilla of the mini pig since the BIV value after 8 weeks is compatible to that of 16 weeks. The osseointegration effect is significantly after 8 weeks, as comparing to untreated implant. After 16 weeks, the osseointegration of the dental implant with the alveolar bone is approaching stable.

According to the table III of resonant frequency securely firm analysis and the table IV of BIV analysis, the summaries are as follows:

1. The mandible is generally having a higher bone density than the maxilla. The lower bone density herein indicates it is D3 or below such as D4 and the higher done density indicated it is D2 or above such as D1. The concept of the bone quality classification is proposed by two scholars Lekholm and Zarb, who classified the bone quality into four groups D1, D2, D3, and D4 based on the amount of cortical bone and trabecular bone.

2. For bone quality D3 and D4, it is found to prompt osseointegration if it is a surface treated implant according to the present invention.

3. For bone quality D1 and D2, it is found that the improvement on osseointegration of the surface treated implant is insignificant while comparing to the untreated implant.

The attached element of the surface treated implants using etching conditions of sample #5 and of the sample #9 are analyzed further by energy dispersion X ray (EDX) to find whether they have something difference. The results are shown in table V.

TABLE V

| 104° C./25 min 60 vol. % HF | | | 25° C./24 h 60 vol. % HF + 40 vol. % H3PO4 | | |
|---|---|---|---|---|---|
| El element | wt % | atomic % | El element | wt % | atomic % |
| O | 34.99 | 75.42 | O | 39.8 | 78.66 |
| Zr | 65.01 | 24.58 | Ca | 1.05 | 0.83 |
| | | | Zr | 59.15 | 20.51 |

The original composition of the zirconia ceramic implant does not contain Ca but elements of Zr and O only. After etching the implant in an etching solution of 60 vol. % HF at 104° C./25 min, the composition is the same as the original. However, it does not while the etching condition is changed to etching conditions of 25° C./24 h 60 vol. % HF+40 vol. % $H_3PO_4$. Since an acid-base neutralization has to be conducted after etching the implants. Thus the calcium element may thus be generated. The surface treated implant contain Ca, may be one of factors to prompt osseointegration.

Subsequently, a further analysis using scanning electron microscopy (SEM) to observe the surface morphology and an α-stepper technique to measure the roughness along the normal of the surface are performed. To facilitate SEM observation and roughness measurement, herein the samples are foregoing zirconia ceramic disk samples #10, #4 and, #5.

Figure 2:
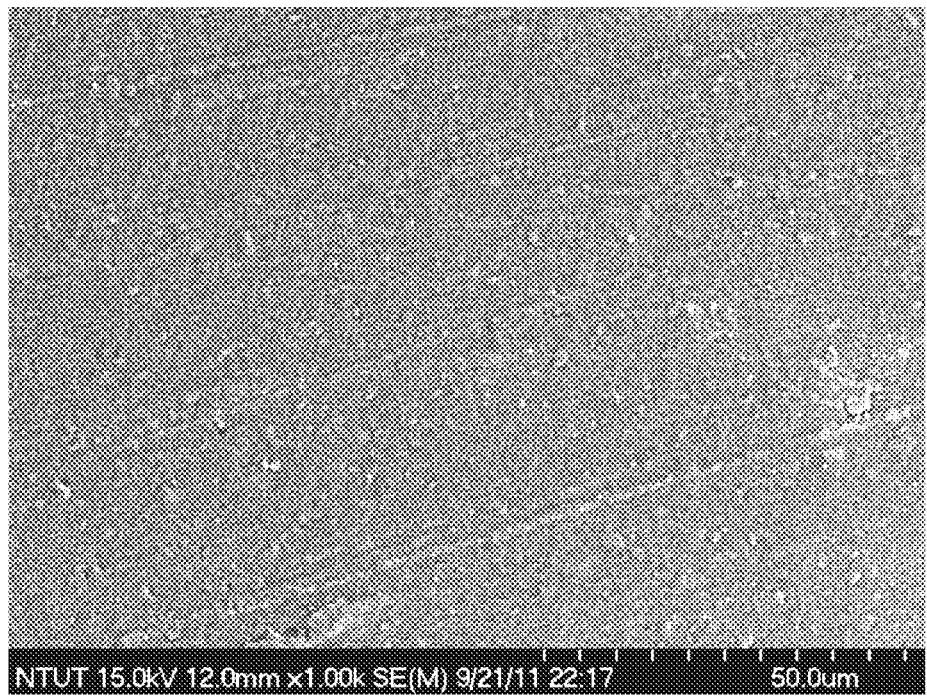
FIG. 2 shows a scanning electron microscopy image of an untreated zirconia ceramic disk.

Please refer to FIG. 2. The SEM image of the untreated zirconia ceramic disk, sample #10, shows it is a rather smooth surface having a few of micro-pits in sizes between about 0.5 μm to 2 μm. A surface roughness along the normal of the surface by α-stepper is carried out. The arithmetic average surface roughness (Ra) is 0.19 μm, standard deviation (STD) is 0.18 μm.

Figure 3:
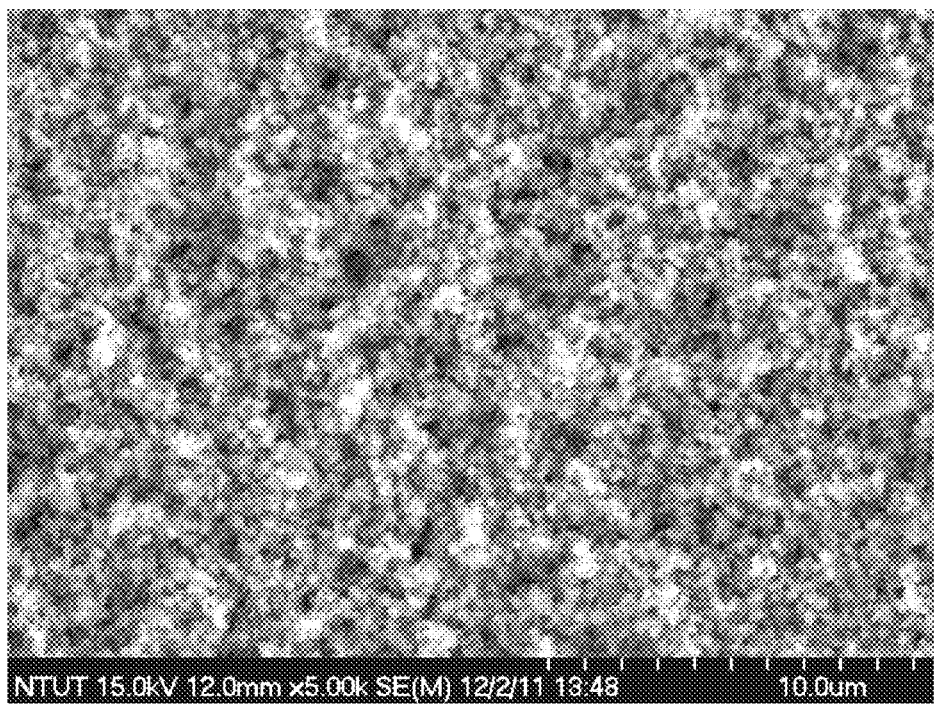
FIG. 3 shows a scanning electron microscopy image of a zirconia ceramic disk after processing a surface treatment of acid etching according to a preferred embodiment of the present invention.

The SEM image of the sample #5, being surface treatment according to the method of the present invention, is shown in FIG. 3. The average surface roughness measured are Ra=0.59 μm, STD=0.12 μm. It means the roughness difference is significant and the roughness distribution is rather even and the results are consistent with the SEM image.

Figure 4:
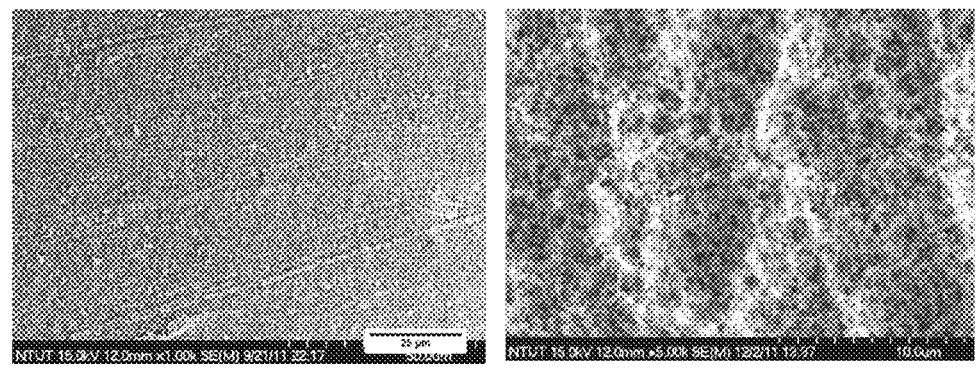
FIG. 4 show a series of scanning electron microscopy images of zirconia disk (i) before surface treatment, (II) after surface treatment by an acidic solution of 60 vol. % HF, (iii) after surface treatment by an acidic solution of 60 vol. % HF and 40 vol. % $H_3PO_4$, and (iM), (iiM), (iiiM) are corresponding enlarge images, respectively.
Figure 4:
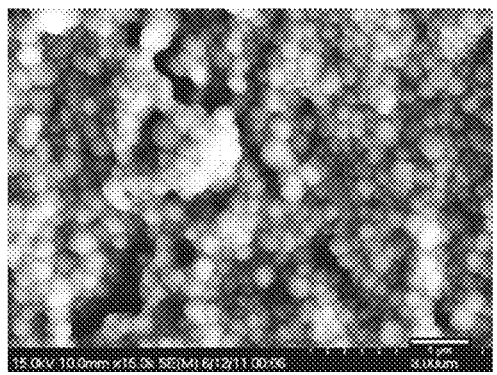
Figure 4:
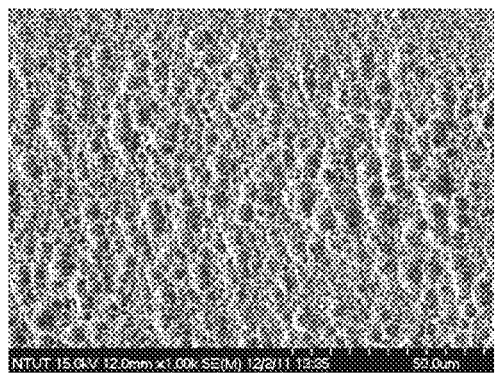
Figure 4:
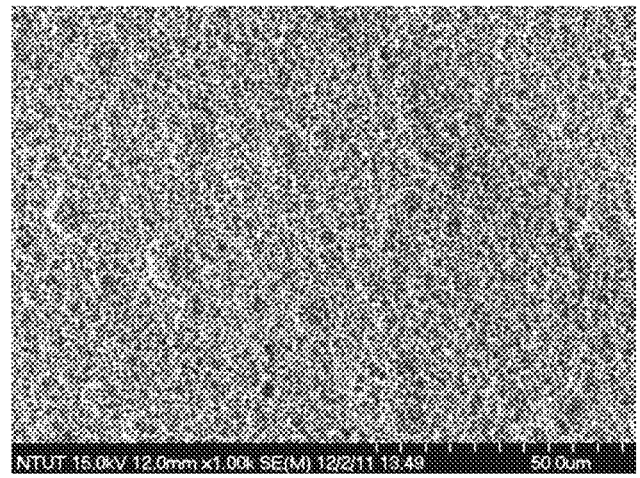
Figure 4:
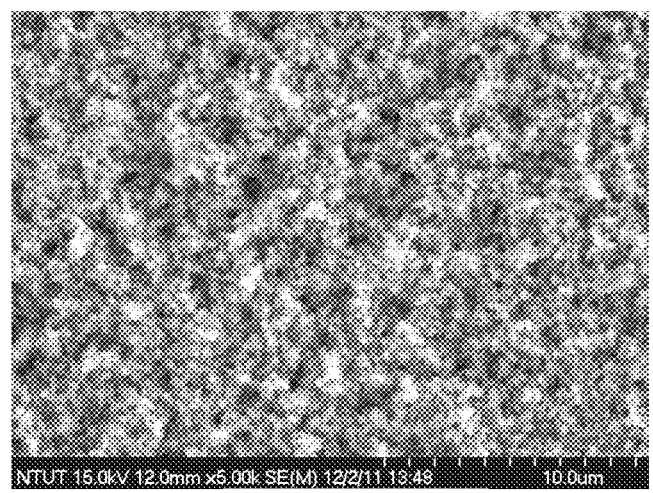

The SEM images of the sample #4 are shown in FIG. 4 (ii). FIG. 4 (iiM) is a SEM with relative high magnification. For antithesis, FIG. 4 lists (i) the SEM images of untreated (sample #10), (ii) the SEM images of treated (sample #4), and (iii) the SEM images of treated (sample #10) and (iM), (iiM), (iiiM) are, respectively, the corresponding SEM images with relative high magnification.

Viewing from the SEM images of the sample #4 shown in FIG. 4 (ii) and FIG. 4 (iiM), the surface morphology shows the undulated surface change is significant. The result is consistent with the contact angle 10.1°, STD 9.9° shown in table I. In the etching process, the relative weak points are etched and concentrated by hydrofluoric acid to form micro-pits and further deepen with the time to become deep tens micrometer deep pits. By contrast, the phenomenon of weak weaker is mitigate and not significant when the etching solution contains 60 vol. % HF and 40 vol. % H3PO4.

Albeit, the foregoing embodiment using 25° C./12 h/24 h as the best mode for the zirconia implant (or disk) is to illustrate conveniently, but not intend to limit thereto. For example for both efficiency and feasibility are concerned, the etching condition according to the present invention, includes (1) using an etching solution HF of about 55~65 vol. %, $H_3PO_4$ of about 20~50 vol. % and $H_2O$ 0~20 vol. % at a temperature between about 15° C.~35° C. for an etching time at least 12 hours. Preferably, the treatment time is between 12~36 hours. The foregoing parameters may be appropriate adjusted so that the result of average contact angle is at most 40° and STD is within 5°. In a best mode, the average contact angle is of 4.3°, and STD is of 1.3°, the etching conditions of sample #5.

The benefits of the present invention are:

(1) to obtain the surface roughness even distribution etching at room temperature is enough.

(2) without sandblasting process as the pretreatment of etching so that the risk of implants being contaminated by the residual abrasive particles is free.

(3) implants with a surface treatment according to the present invention is found to shorten hearing period, in particularly to beneficial to those bone quality classified as D3 or D4 in accordance with the results of the resonant frequency security firm analysis and BIV analysis As is understood by a person skilled in the art, the foregoing preferred embodiments of the present invention are illustrated from the present invention rather than limiting of the present invention. It is intended to cover various modifications and similar arrangements included within the spirit and scope of the appended claims, the scope of which should be accorded the broadest interpretation so as to encompass all such modifications and similar structures.

What is claimed is:

1. A method of surface treatment of a zirconia ceramic implant, comprising the steps of:
   providing an implant formed of zirconia powder pressed in a mold and sintered; and
   etching the implant in an etching solution at an etching temperature between about 15~35° C. for an etching time at least 12 hours, wherein a composition of said etching solution consisting of a mixture of HF 50~65 vol. %, $H_3PO_4$ 20~45 vol. %, and $H_2O$ 0%~20 vol. %.

2. The method according to claim 1, before the step of etching said implant, further comprises a pretreatment step of grease removal for said implant without any sandblasting or milling process.

3. The method according to claim 1, before the step of etching, an average contact angle of said implant is at least 90°.

4. The method according to claim 1 wherein said composition of said etching solution comprises a mixture of HF 58~62 vol. %, $H_3PO_4$ 32~43 vol. %, and water 0~10 vol. % at a temperature between about 15~30° C. for 12~36 hours.

5. The method according to claim 1 wherein an inner surface of said mold is a surface without any roughness treatment except having a shape of said implant.

6. The method according to claim 1 wherein said implant has an average contact angle smaller than 40° after the step of etching.

7. The method according to claim 1 wherein said implant has an average contact angle smaller than 10° after the step of etching.

8. A method of surface treatment of a zirconia ceramic implant, comprising the steps of:
   providing an implant formed of zirconia powder pressed in a mold and sintered, wherein an inner surface of said mold haven't macroscopic roughness formed thereon;
   processing an pretreatment for said implant to remove any grease, wherein said pretreatment process does not include any sandblasting or milling process; and
   etching the implant in an etching solution at an etching temperature between about 15~35° C. for an etching time at least 12 hours, wherein a composition of said etching solution comprises a mixture of HF 50~65 vol. %, $H_3PO_4$ 20~45 vol. %, and $H_2O$ 0%~20 vol. %.

* * * * *